United States Patent
Eckhardt et al.

(10) Patent No.: US 11,559,645 B2
(45) Date of Patent: Jan. 24, 2023

(54) VENTILATION SYSTEM WITH ELECTROCHEMICAL FILTER FOR ALKYL PHENOLS AND METHOD USING THE ELECTROCHEMICAL FILTER

(71) Applicant: Drägerwerk AG & Co. KGaA, Lübeck (DE)

(72) Inventors: Rolf Eckhardt, Hamburg (DE); Christel Birkmann-Little, Frankfurt am Main (DE)

(73) Assignee: Drägerwerk AG & Co. KGaA, Lübeck (DE)

(*) Notice: Subject to any disclaimer, the term of this patent is extended or adjusted under 35 U.S.C. 154(b) by 412 days.

(21) Appl. No.: 16/507,775

(22) Filed: Jul. 10, 2019

(65) Prior Publication Data
US 2020/0016354 A1    Jan. 16, 2020

(30) Foreign Application Priority Data
Jul. 11, 2018   (DE) .......................... 102018005450.1

(51) Int. Cl.
*A61M 16/00*    (2006.01)
*G01N 33/00*    (2006.01)
(Continued)

(52) U.S. Cl.
CPC .......... *A61M 16/026* (2017.08); *A61M 16/22* (2013.01); *G01N 30/02* (2013.01);
(Continued)

(58) Field of Classification Search
CPC ................ A61M 16/026; A61M 16/22; A61M 2016/1035; A61M 2202/0241; A61M 2205/75; A61M 16/024; A61M 16/105; A61M 16/0066; A61M 16/0081; A61M 16/01; A61M 16/0891; A61M 16/208;
(Continued)

(56) References Cited

U.S. PATENT DOCUMENTS

| 6,607,642 B1 * | 8/2003 | Kiesele | ................ G01N 27/308 |
| | | | 204/415 |
| 2005/0022811 A1 * | 2/2005 | Kiesele | ................ A61M 16/01 |
| | | | 128/203.14 |

(Continued)

FOREIGN PATENT DOCUMENTS

| CN | 101362677 A | 2/2009 |
| CN | 106461593 A | 2/2017 |

(Continued)

OTHER PUBLICATIONS

Langmaier J. et al., Electrochemical quantification of 2,6-diisopropylphenol (propofol), Journal, 2011, 63-67, 704, Elsevier, Netherlands.

(Continued)

*Primary Examiner* — Kendra D Carter
*Assistant Examiner* — Arielle Wolff
(74) *Attorney, Agent, or Firm* — McGlew and Tuttle, P.C.

(57) ABSTRACT

A ventilation system includes an electrochemical filter for depleting alkyl phenols, especially 2,6-diisopropyl phenol, in breathing gas. A method uses the filter for removing alkyl phenols, especially 2,6-diisopropyl phenol, from breathing gas.

20 Claims, 2 Drawing Sheets

(51) Int. Cl.
  *A61M 16/22* (2006.01)
  *G01N 30/02* (2006.01)
  *A61M 16/10* (2006.01)
(52) U.S. Cl.
  CPC . *G01N 33/0047* (2013.01); *A61M 2016/1035* (2013.01); *G01N 2030/025* (2013.01)
(58) Field of Classification Search
  CPC .............. A61M 16/201; A61M 16/085; A61M 2016/0027; A61M 16/0003; G01N 33/0047; G01N 30/02; G01N 2030/025; G01N 27/28; G01N 27/30; G01N 27/308; G01N 33/497; G01N 27/3277; G01N 27/403–404; G01N 33/15; G01N 33/0004; G01N 27/4045; G01N 27/4162; G01N 33/0014; G01N 1/2205; B01D 2259/4533; B01D 53/04; B01D 53/30; B01D 2253/1122; B01D 53/326; B01D 53/323; A61B 5/097; A61B 5/082; A61B 5/4821; B03C 3/011; B03C 3/017; B03C 2201/26
  See application file for complete search history.

(56) References Cited

U.S. PATENT DOCUMENTS

| | | |
|---|---|---|
| 2008/0077080 A1 | 3/2008 | Hengstenberg et al. |
| 2009/0281443 A1 | 11/2009 | Hengstenberg et al. |
| 2012/0277613 A1* | 11/2012 | Li .................... A61B 5/082 600/532 |
| 2016/0213879 A1* | 7/2016 | Parthasarathy ..... A61M 16/208 |
| 2017/0082569 A1* | 3/2017 | Sommer ............... C01B 32/194 |
| 2018/0114649 A1* | 4/2018 | Ng ...................... H01G 9/2018 |

FOREIGN PATENT DOCUMENTS

| | | |
|---|---|---|
| DE | 10335236 B3 | 2/2005 |
| DE | 102006045014 A1 | 4/2008 |
| DE | 102008022761 B4 | 11/2015 |

OTHER PUBLICATIONS

Trhormann et al., Narkosesytem, Article, May 2017, 1-5, Wikipedia, Germany.

* cited by examiner

VENTILATION SYSTEM WITH ELECTROCHEMICAL FILTER FOR ALKYL PHENOLS AND METHOD USING THE ELECTROCHEMICAL FILTER

CROSS REFERENCE TO RELATED APPLICATIONS

This application claims the benefit of priority under 35 U.S.C. § 119 of German Application 102018005450.1, filed Jul. 11, 2018, the entire contents of which are incorporated herein by reference.

TECHNICAL FIELD

The present invention pertains to a ventilation system with an electrochemical filter for depleting alkyl phenols, especially 2,6-diisopropyl phenol, in breathing gas, and to the use of the filter for removing alkyl phenols, especially 2,6-diisopropyl phenol, from breathing gas.

TECHNICAL BACKGROUND 2,6-Diisopropyl phenol (also called propofol) is an intravenously administered hypnotic, which is frequently administered for sedation and for suppressing consciousness during examinations and surgical procedures.

Furthermore, it is known that a patient is provided during anesthesia with a ventilation system, which monitors the breathing of the patient during the anesthesia, e.g., with a rebreathing system, in which the exhaled breathing gas of the patient is again returned to the patient after a processing step, which usually includes the depletion of carbon dioxide.

SUMMARY

To check the effectiveness of anesthesia, it may be desirable to detect the propofol concentration in the breathing gas. However, no accumulation of the anesthetic, which distorts the propofol concentration and leads to supposedly higher values compared to the real ones, may take place for this in the ventilation system. The above-described problem has not been mentioned in the literature so far. This is due mainly to the fact that there is no simple, practical commercially available method for detecting propofol in the breathing gas of a patient during a surgical procedure or medical treatment, especially if breathing apparatuses are used. However, a measuring apparatus for GC-IMS measurements, which is intended for use in operating systems, has currently been introduced on the market by the company B. BRAUN Melsungen. The apparatus is available under the name EDMON and, according to data provided by the manufacturer, it can determine the propofol concentration in the exhaled air of patients who were sedated or anesthetized intravenously by means of propofol. It will be possible to determine whether the concentration in the exhaled air rises, drops or remains constant.

A ventilation system is advantageously provided having an electrochemical cell for oxidizing alkyl phenols, especially a rebreathing system, where the exhaled breathing gas is returned again to the patient after a processing step, which comprises the depletion of carbon dioxide at an absorber. The absorber comprises, e.g., a composition containing calcium hydroxide, e.g., a breathing lime. It was found that propofol can be detected in the breathing gas in the ppb range during a surgical procedure or medical examination, which involves the intravenous use of propofol, and this property can be used to monitor the propofol concentration, especially the drop in this concentration over time. This information can be used to control and monitor the recovery of consciousness of the patient or, on the other hand, to guarantee a steadily sufficient sedation or anesthesia.

It was, however, observed that if a rebreathing system, which is provided with a measuring set-up for monitoring the propofol concentration, is used during a surgical procedure or medical examination, and the breathing gas is drawn off continuously, both inhaled and exhaled gas is drawn through the measuring set-up. Even though propofol occurs in the breathing in the ppb range only, enrichment of propofol in the ventilation system was observed during prolonged operation of the rebreathing system. This causes the measured signal to be influenced not only by propofol from the breathing gas of the patient, as desired, but also by propofol that was retarded by the machine and is then rebreathed.

A stable measured value cannot be obtained for the analyte under these circumstances. Attempts to bind propofol by physisorption on filters or to fix this by a chemical reaction on filter surfaces were unsuccessful. It is very difficult to bond the hydroxyl group irreversibly due to the steric shielding of the isopropyl groups. After an initial physisorption on the surface, desorption of propofol takes place as time progresses or the temperature rises. In addition, it is a requirement that an additional filter in the breathing system must not lead to an increase in the pressure in the system, i.e., the breathing resistance of the filter must be as low as possible. Other anesthetics, which are frequently administered together with propofol, must not be retained or influenced by the filter in terms of their concentration. The sampling for the gas-measuring technique is advantageously carried out on the side of the patient filter facing away from the patient in order to avoid contamination of the rebreathing system with germs from the patient.

The solution of the problem is surprisingly to provide an electrochemical cell, which is swept by the breathing gas, in the ventilation system. While passing over the electrodes of the electrochemical cell, the propofol undergoes an electrochemical reaction and is thus removed from the gas stream. The electrochemical cell acts as a filter. The peculiarity of this filter is, furthermore, that it can be switched electrically, i.e., the filter can be switched on when needed (by applying a potential difference) and its effect can thus be utilized, or it can be left switched off. It has no filter effect in the second case. This is at first a surprising fact, because electrochemical electrodes, as they are also used, for example, in sensors, always bring about a catalytic reaction of analyte. Thus, it is not possible, for example, to operate a CO sensor without CO being reacted at it, even when it is "formally" switched off.

The filter according to the present invention is an electrochemical cell, through which the path of the gas is routed such that the gas sweeps over the surface of a working electrode. The working electrode is connected, e.g., to a counterelectrode as well as to a reference electrode via a second-order conductor. The working electrode is maintained by the reference electrode or a potentiostat connected to same at a working potential of 100-500 mV.

The alkyl phenol, such as propofol, is electrochemically oxidized at this potential and is thus removed from the gas stream. The electric current is not transported in a second-order conductor by the motion of electrons, unlike in metals, but by ionic motions.

The electrodes may comprise each one or more precious metals or also consist of carbon in different modifications. In addition to platinum, carbon, especially "glassy carbon," DLC (diamond like carbon), MW-CNT (multiwall carbon nanotubes), activated carbon, graphene or reduced graphene oxide, is suitable above all, graphene being preferred.

A salt solution, such as an aqueous sulfuric acid, is used as the electrolyte. The electrolyte itself may be liquid, in the form of a gel, or a porous solid impregnated with the electrolyte.

The sensor is configured analogously to a typical three-electrode (3E) electrochemical gas sensor. It comprises a working electrode, a reference electrode and a counterelectrode. The gas is reacted oxidatively at the working electrode. A reduction, in this case that of oxygen, takes place at the counterelectrode. The reference electrode maintains the reference voltage on the working electrode, but no current flows through it itself. The working electrode consists of catalytically active materials, as they were described in more detail above, optionally pressed onto an open-pore hydrophobic membrane. This membrane then forms with the electrolyte a large surface, which is in contact with gas. A thin, gas-permeable electrolyte film, through which gas can diffuse to the electrode material, is formed on the hydrophilic catalyst. The material of the counterelectrode is not so important. The working electrode is polarized by applying an external voltage (see above, 100-500 mV) against the counterelectrode.

In addition to the propofol being described here:

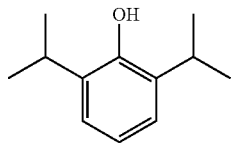

it is also possible to remove other alkyl phenols, especially those containing 1 to 3 alkyl substituents and, in terms of the sum of all alkyl substituents, 1 to 12 carbon atoms, preferably totaling 3 to 8, by the electrical cell being described here.

The filter was tested in different configurations. In the sleeve configuration, the filter contains a large electrode, over which the gas stream is sent. In order to guarantee the residence time of propofol in the filter even in case of high throughputs of air, an absorbent with a large inner surface, on which the propofol can be deposited, can be added. For example, activated carbon or silicon dioxide (trade name Sipernat® or Sident®, both by EVONIC SE), are preferred here, the commercially available product Sipernat® 500 of EVONIC SE being preferred.

The filters maybe operated at room temperature or even at elevated temperature. The reaction on the filter increases slightly with rising temperature and so is the rate at which the propofol is decomposed.

The present invention will be explained in more detail by the figures, without being limited to these. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
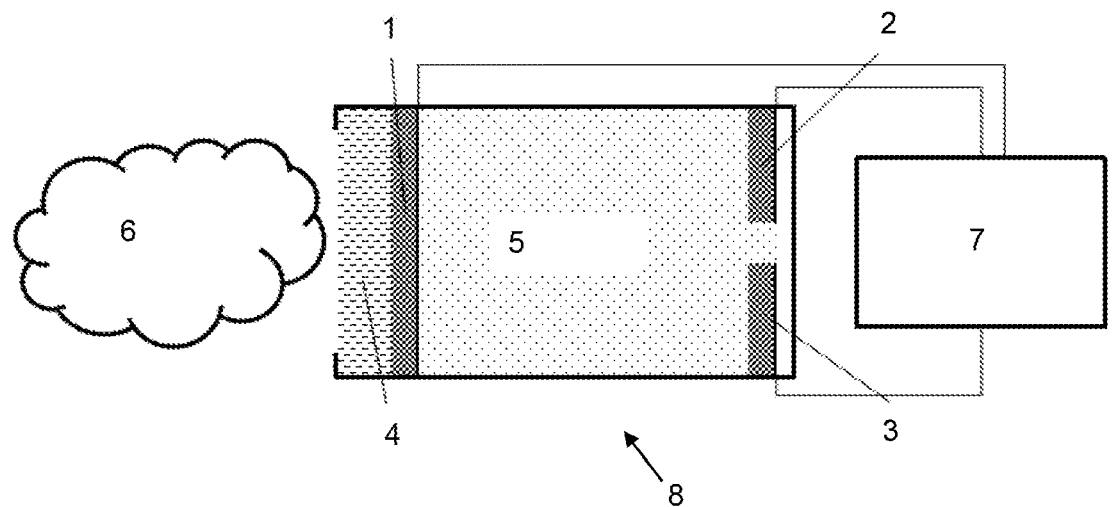
FIG. 1 is a schematic view of an electrochemical cell.

Referring to the drawings, FIG. 1 shows a schematic functional diagram of the electrochemical cell (filter 8) used according to the present invention, which corresponds to that of an electrochemical gas sensor. The configuration of the cell from a membrane 4, working electrode 1 wetted by electrolyte, counterelectrode 2, reference electrode 3 and potentiostatic circuit 7 for applying a constant voltage in the range of 100 mV to 500 mV to the working electrode are illustrated in particular. Propofol reaches the working electrode 1 from the breathing air 6 and is oxidized there. This causes a current. The sensor has the same configuration as the filter from FIG. 1, but it is configured for smaller gas streams, and the current proportional to the propofol concentration is measured.

Figure 2:
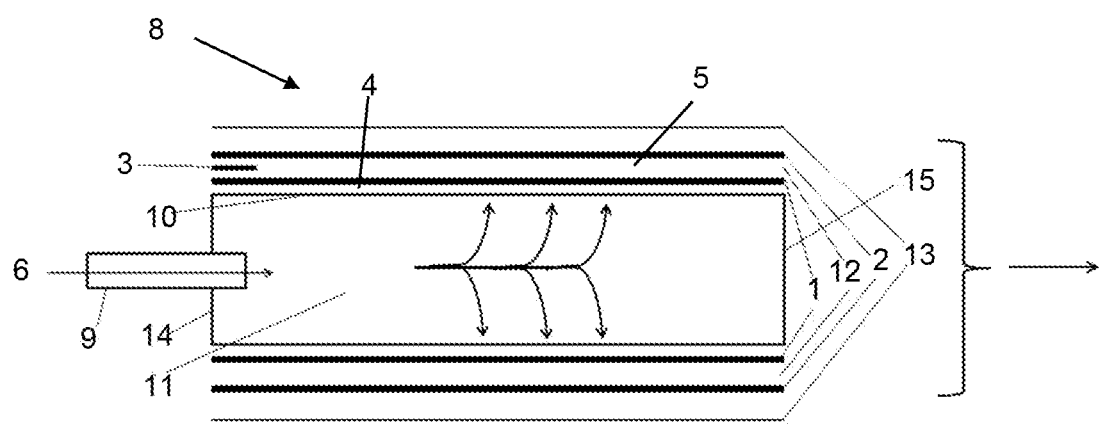
FIG. 2 is a schematic view showing a configuration of the filter in the form of a filter sleeve, through which breathing air can flow.

FIG. 2 shows a configuration of a filter 8. Propofol-containing gas 6 flows through the inlet 9 into the filter sleeve 10. The sleeve 10 is filled with an adsorbent 11. The gas 6 permeates through the sleeve 10 and reaches the working electrode 1, which surrounds the filter sleeve 10 in a cylindrical form. The second-order conductor 12 and the reference electrode 3 are located between the working electrode 1 and the counterelectrode 2. The filter 8 is sealed towards the outside with a film 13 in order to prevent the electrolyte from escaping. The filter sleeve 10 is closed at the beginning 14 and at the end 15, so that the gas 6 is sent over the electrode 1. The electrodes are contacted (not shown) with a potentiostat, which supplies the bias voltage for the working electrode 1. The use of the adsorbent 11 leads to a certain filter effect. However, the removal of propofol is guaranteed by the working electrode 1 only, and it thus prevents the repeated release and enrichment of propofol in the system. An advantage of this configuration is the large inner surface of the filter 8, which guarantees a high mass throughput through this, without significantly increasing the flow resistance. It is also possible to connect a plurality of such filters 8 in series or in parallel.

By measuring the conversion currents in µA, it is possible in this configuration to monitor how the filter operates and how high its utilization is. Different propofol concentrations in the measured gas lead to different conversion currents in the filter, but above all in the first partial filter, when a plurality of filters are connected in series. A propofol concentration of 40-90 ppb can be retained with certainty.

Figure 3:
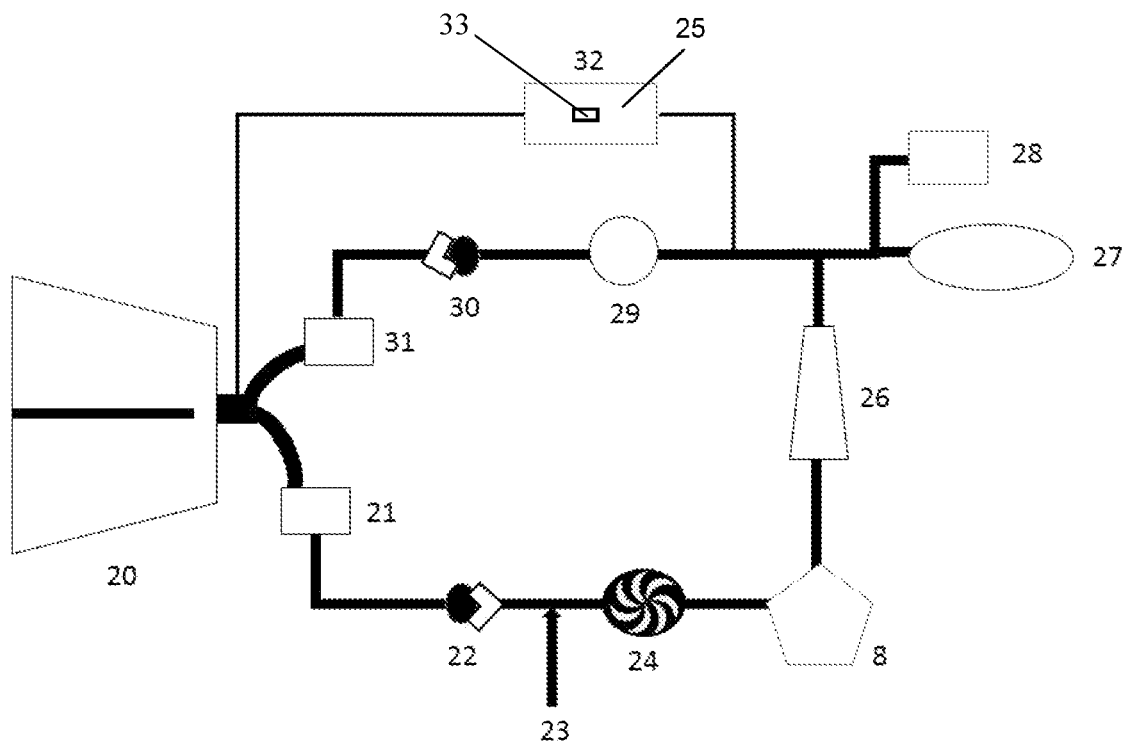
FIG. 3 is a schematic view showing a ventilation system with the filter.

The only thing to which attention should be paid in the rebreathing system of a ventilator is that the propofol filter be located behind the patient filter in order not to become contaminated with germs itself, see the bottom part of FIG. 3. The filter should also rather be located far away from the patient or the Y-piece in order not to hinder this or the medical staff.

During operation of patients under full anesthesia, the patients must usually be ventilated, because anesthetics have a depressive effect on breathing. Ventilators, in which the breathing air of the patient is processed and is returned to the patient, are frequently used for this purpose.

Such a closed-circuit breathing system shown in FIG. 3 includes a breathing gas flow arrangement. The exhaled air of the patient/breathing person 20 is breathed into the expiratory branch of the closed ventilation circuit via an expiratory pressure sensor 31. The flow direction is preset by corresponding nonreturn valves 30, 22 on the expiratory side and on the inspiratory side. The PEEP (Positive End Expiratory Pressure) valve 29 maintains a defined back pressure in relation to the lungs of the patient 20 and thus prevents the pulmonary alveoli from collapsing during the ventilation. Gas is continuously removed from the breathing air via a bypass and tested for its components in a gas-measuring bank 32. These are, on the one hand, the breathing gases carbon dioxide and oxygen, which offer direct information on the vital functions of the patient, but also anesthetics. Volatile anesthetics and oxygen can be returned in this manner into the breathing gas stream via the side inlet 23 in a controlled manner and as needed. The injected hypnotic propofol from the patient's breath is measured at the measuring point 25, which is arranged where the gas-measuring bank 32 is located, so that the propofol sensor is part of the gas-measuring bank 32, and the degree of sedation of the patient is thus checked. However, any other desired measuring point is possible as well.

If the control 28 does not detect any spontaneous breathing of the patient, the blower 24 ensures external ventilation. As an alternative, it is still always possible to ventilate the patient with a manual bellows 27. The exhaled carbon dioxide is removed from the breathing gas by means of a breathing lime cartridge 26. The breathing air is then fed again to the patient via the inspiratory pressure sensor 21 after adding oxygen and possibly anesthetic gas via the side inlet 23. The switchable electrochemical phenol sensor according to the present invention is a filter 8 and represents an infinite sink for propofol and it thus prevents the hypnotic from becoming enriched in the ventilation system and thus from also distorting the measurement in the gas-measuring bank 32 and hence regulation of the patient's anesthesia. If no propofol is used for the anesthesia, the filter 8 can remain switched off and thus it is not active any longer.

While specific embodiments of the invention have been shown and described in detail to illustrate the application of the principles of the invention, it will be understood that the invention may be embodied otherwise without departing from such principles.

APPENDIX

List of Reference Designations

| | |
|---|---|
| 1 | Working electrode |
| 2 | Counterelectrode |
| 3 | Reference electrode |
| 4 | Membrane |
| 5 | Electrolyte |
| 6 | Breathing air/gas with alkyl phenol |
| 7 | Measuring electronic unit/potentiostatic circuit |
| 8 | Filter |
| 9 | Inlet into the filter sleeve |
| 10 | Filter sleeve |
| 11 | Adsorbent |
| 12 | Second-order conductor |
| 13 | Film |
| 14 | Beginning of the filter sleeve |
| 15 | End of the filter sleeve |
| 20 | Patient |
| 21 | Inspiratory pressure sensor |
| 22 | Nonreturn valve in the inspiratory branch |
| 23 | Side inlet |
| 24 | Circulator/blower |
| 25 | Measuring point for propofol |
| 26 | Breathing lime cartridge |
| 27 | Manual bellows |
| 28 | Control |
| 29 | PEEK valve |
| 30 | Nonreturn valve in the expiratory branch |
| 31 | Expiratory pressure sensor |
| 32 | Gas-measuring bank |

What is claimed is:

1. A ventilation system comprising:
a breathing gas flow arrangement through which a breathing gas containing an alkyl phenol flows; and
an electrochemical cell with electrodes as an absorption filter having an absorbent for filtering the alkyl phenol from the breathing gas, wherein the electrochemical cell comprises a filter sleeve containing the absorbent, wherein an electrical potential is applied to the electrodes for oxidation of the alkyl phenol for removing the alkyl phenol from the breathing gas, wherein the absorbent for the alkyl phenol is comprised of activated carbon and/or a silicon dioxide, the electrodes comprising a working electrode, a counterelectrode and a reference electrode, the electrochemical cell further comprising a second-order conductor, wherein the breathing gas sweeps over the working electrode, the working electrode being connected via the second-order conductor to the counterelectrode, whereby the working electrode is maintained by the reference electrode or by a potentiostat connected to the reference electrode at a working potential of 100 mV to 500 mV.

2. A ventilation system in accordance with claim 1, wherein the breathing gas flow arrangement comprises a rebreathing circuit system with a carbon dioxide absorber and an exhaled breathing gas is returned again to a breathing person after a processing step, wherein the processing step comprises depletion of carbon dioxide at the carbon dioxide absorber, wherein the electrochemical cell defines a gas flow path.

3. A ventilation system in accordance with claim 2, wherein the carbon dioxide absorber contains calcium hydroxide.

4. A ventilation system in accordance with claim 1, wherein the alkyl phenol has 1 to 3 alkyl substituents and the alkyl substituents have a total of 1 to 12 carbon atoms.

5. A ventilation system in accordance with claim 4, wherein the alkyl phenol comprises propofol, wherein a concentration of the propofol is determined based on the oxidation of the alkyl phenol.

6. A ventilation system in accordance with claim 1, wherein a concentration of alkyl phenol for breathing gas is 1 ppb to 100 ppb.

7. A ventilation system in accordance with claim 1, further comprising a sensor for determining a concentration of the alkyl phenol.

8. A ventilation system in accordance with claim 1, wherein the electrochemical cell has an electrical power connection for applying an electrical potential to the electrodes to form a switchable filter, which can be switched electrically on and off, wherein the oxidation of the alkyl phenol occurs when the switchable filter is electrically on.

9. A ventilation system in accordance with claim 1, wherein the electrodes each comprise one or more precious metals, carbon and graphene.

10. A ventilation system in accordance with claim 1, wherein the working electrode is arranged on an open-pore hydrophobic membrane, and the open-pore hydrophobic membrane forms a surface that is in contact with gas with an electrolyte.

11. An electrochemical cell method comprising:
providing an electrochemical cell with electrodes to form an absorption filter having an absorbent for filtering alkyl phenol, wherein the electrochemical cell comprises a filter sleeve containing the absorbent, wherein the absorbent for the alkyl phenol is comprised of activated carbon and/or a silicon dioxide, the electrodes comprising a working electrode, a counterelectrode and a reference electrode, the electrochemical cell further comprising a second-order conductor, wherein breathing gas sweeps over the working electrode, the working electrode being connected via the second-order conductor to the counterelectrode, whereby the working electrode is maintained by the reference electrode or by a potentiostat connected to the reference electrode at a working potential of 100 mV to 500 mV; and applying an electrical potential to the electrodes for the oxidation of the alkyl phenol for removing the alkyl phenol from the breathing gas.

12. An electrochemical cell method according to claim 11, further comprising connecting the electrochemical cell to a ventilation system comprising a breathing gas flow arrangement through which the breathing gas containing the alkyl phenol flows.

13. An electrochemical cell method in accordance with claim 12, wherein the breathing gas flow arrangement comprises a rebreathing circuit system with a carbon dioxide absorber and the exhaled breathing gas is returned again to the breathing person after a processing step, which processing step comprises the depletion of carbon dioxide at the carbon dioxide absorber.

14. An electrochemical cell method in accordance with claim 13, wherein the carbon dioxide absorber contains calcium hydroxide.

15. An electrochemical cell method in accordance with claim 12, wherein the alkyl phenol comprises propofol, wherein a concentration of the propofol is determined based on the oxidation of the alkyl phenol.

16. An electrochemical cell method in accordance with claim 12, further comprising providing a sensor for determining a concentration of the alkyl phenol.

17. An electrochemical cell method in accordance with claim 11, wherein the electrochemical cell has an electrical power connection for applying an electrical potential to the electrodes to form a switchable filter, which can be switched electrically on and off, wherein the oxidation of the alkyl phenol occurs when the switchable filter is electrically on, wherein the electrochemical cell defines a gas flow path.

18. An electrochemical cell method comprising: providing an electrochemical cell comprising an absorbent, a second-order conductor, a working electrode, a counterelectrode and a reference electrode, wherein the electrochemical cell comprises a filter sleeve containing the absorbent, the absorbent being comprised of activated carbon and/or a silicon dioxide, the working electrode being configured to contact breathing gas comprising alkyl phenol, the absorbent filtering the alkyl phenol from the breathing gas, the working electrode being connected via the second-order conductor to the counterelectrode; and applying an electrical potential to the electrodes for oxidation of the alkyl phenol such that the alkyl phenol is removed from the breathing gas via the electrochemical cell.

19. An electrochemical cell method according to claim 18, wherein the working electrode is maintained by the reference electrode or by a potentiostat connected to the reference electrode at a working potential of 100 mV to 500 mV.

20. An electrochemical cell method according to claim 19, further comprising connecting the electrochemical cell to a ventilation system comprising a breathing gas flow arrangement through which the breathing gas containing the alkyl phenol flows.

* * * * *